(12) United States Patent
Fischer

(10) Patent No.: US 8,226,877 B2
(45) Date of Patent: Jul. 24, 2012

(54) DECIDUOUS DENTITION JEWELRY AND METHOD OF MANUFACTURE

(75) Inventor: John G. Fischer, Irving, TX (US)

(73) Assignee: Shawdon, LP, Irving, TX (US)

( * ) Notice: Subject to any disclaimer, the term of this patent is extended or adjusted under 35 U.S.C. 154(b) by 0 days.

(21) Appl. No.: 12/699,476

(22) Filed: Feb. 3, 2010

(65) Prior Publication Data
US 2011/0187024 A1 Aug. 4, 2011

(51) Int. Cl.
B29C 33/40 (2006.01)
A44C 25/00 (2006.01)
A47G 33/04 (2006.01)

(52) U.S. Cl. ............ 264/337; 264/16; 63/33; 63/36; 428/7

(58) Field of Classification Search ............ 264/337, 264/16; 66/33, 36; 428/7
See application file for complete search history.

(56) References Cited

U.S. PATENT DOCUMENTS

| 5,755,116 A | * | 5/1998 | Sparacino et al. ............ 63/3 |
| 5,762,502 A | * | 6/1998 | Bahn et al. ............ 433/215 |
| 6,200,507 B1 | * | 3/2001 | Dennis ............ 264/73 |
| 7,228,602 B2 | * | 6/2007 | Weisbrot et al. ............ 27/1 |
| 2002/0025392 A1 | * | 2/2002 | Yardley et al. ............ 428/3 |
| 2003/0194678 A1 | * | 10/2003 | Viltro et al. ............ 433/80 |
| 2008/0053149 A1 | * | 3/2008 | Benos ............ 63/35 |

FOREIGN PATENT DOCUMENTS

| JP | 2002-219009 | * | 8/2002 |
| JP | 2006-255367 | * | 8/2005 |
| TW | 200819092 | * | 5/2008 |

OTHER PUBLICATIONS

Human Teeth Jewelry, http://www.stylelist.com/2007/05/22/human-teeth-jewelry/, published Aug. 22, 2007.*

* cited by examiner

*Primary Examiner* — Yogendra Gupta
*Assistant Examiner* — Jeremiah Smith

(57) ABSTRACT

The invention discloses jewelry made of pulverized and recombined primary human teeth, or baby teeth. The human deciduous dentin are partially pulverized and bonded with a chemical bonding agent in a frame configured to receive the pulverized dentin mold or pre-formed frame to create designs personalized to the family members.

22 Claims, 2 Drawing Sheets

DECIDUOUS DENTITION JEWELRY AND METHOD OF MANUFACTURE

CROSS-REFERENCES TO RELATED APPLICATIONS

None

BACKGROUND OF THE INVENTION

1. Technical Field

The present invention relates to jewelry, and more particularly to a jewelry made of human bone. Specifically, the preferred embodiment discloses jewelry made of pulverized and recombined primary human teeth, or baby teeth. When a parent saves the baby teeth of his/her children, the teeth would be partially or fully pulverized and bonded with a chemical bonding agent in a mold or pre-formed frame to create designs personalized to the family members.

2. Description Of Related Art

None

2. Background Information

Jewelry made from the bones and teeth of animals has been known and made and worn in early civilizations. From shark teeth to bear claws, man has adorned his body with animal tissue for both necessity and vanity since before written history. Even today, shark teeth are a popular necklace. It is believed the Vikings may have made jewelry from human teeth. It has also been known to string teeth together for attachment to a necklace. It has also been known in Costa Rica and Chile to set the solid deciduous dentition pieces in gold or silver, to make a necklace or earring.

What has not known to have been done is to manufacture jewelry from processed human deciduous dentition, as in the manner disclosed. The hardest thing in the human body is the enamel on the teeth. Like all mammals, humans have primary teeth and permanent teeth. Teeth begin being formed before birth.

Human teeth are very hard in order to withstand the grinding forces associated with chewing and crunching food. The hard material of the tooth is composed of calcium, phosphorus and other mineral salts. The material in the majority of the tooth is called dentine. The hard, shiny exterior layer is the enamel.

Teeth have two basic parts; a root to anchor the tooth to the jaw and a crown above the gum line. The root is covered with a hard material called cementum. At the center of each tooth is an area with nerves, arteries and veins called the dental pulp.

Humans have four different types of teeth, each with a different function: Incisors for cutting off bites of food; cuspids (with long sharp points) for tearing food; bicuspids (with two points) to tear and crush food; and molars with large, relatively flat surfaces to crush and grind food.

The four types of teeth together allow humans to be omnivores (eating both meat and vegetables). Most animals have more specialized teeth. Carnivorous (meat eating) animals have long sharp tearing teeth. Grazing animals, like cows and horses, have large flat teeth for grinding grass and other vegetation. Deciduous dentition is also known as the primary, baby, milk, or lacteal dentition.

The term deciduous means "to fall off." Although deciduous teeth are in time replaced by the succedaneous, or permanent, teeth, they are very important to the proper alignment, spacing and occlusion of the permanent teeth. The deciduous incisor teeth are functional in the mouth for approximately five years, while the deciduous molars are functional for approximately nine years. They therefore have considerable functional significance. The progressive loss of deciduous teeth are considered an important milestone in the developmental phase of childhood.

The events are often marked by celebration, traditions and superstitions around the world. In the United States, tradition is based on tales of the Tooth Fairy. In Australia, mothers are once believed to have crushed their children's baby teeth and eaten the powder.

In some parts of the world, a child's baby tooth was placed in nests where rats or snakes were known to live because people believed evil witches disliked those animals and wouldn't go near them. In many parts of the world, parents placed their children's teeth in mouse nests. They thought that would result in a new tooth growing in the lost tooth's place, just as a mouse's lost teeth somehow re-grew.

In other parts of the world, mothers hid their children's teeth from animals because they believed if an animal found the tooth, a tooth like that animal's would grow in the mouth of the child.

In parts of England, mothers at one time burned their children's baby teeth so that evil witches couldn't get their hands on them and gain control of the children.

It is common for parents to save, at least for a while, the deciduous teeth of their children as a keepsake of their childhood and development. The typical storage means is a small envelope or decorative box. One disadvantage of this method of saving deciduous teeth is that the deciduous teeth are biologically contaminated. Another problem is that a small box filled with tiny teeth isn't significant as a keepsake, other than the origin of the bone matter itself.

Another disadvantage of storing deciduous teeth is that the collective individual teeth are easily lost or mixed up with the teeth of other children. Another disadvantage of storing deciduous teeth is they lack the display appeal of photographs, gifts, letters, and other memorabilia.

BRIEF SUMMARY OF THE INVENTION

The history of jewelry is as old as the history of man. Styles and trends come and go and come again. What is not found in this history is any event of persons wearing the human bone of their family members in the form of jewelry. Indeed, the notion sounds barbaric and contrary to civilized norms. However, the inventor believes that it could symbolize the ultimate commitment of love and devotion a parent can have for a child. The symbol exceeds the relevance of personal adornment, much as a Christian wearing a cross.

A primary advantage of the present invention is that it creates a new material form of jewelry. Another advantage of the present invention is that it creates a symbolic means of displaying family commitment in the form of jewelry. Another advantage of the present invention is that it provides multiple and virtually unlimited opportunities to display the symbols. Another advantage of the present invention is that it provides a value added means of keeping family baby teeth. Another advantage of the present invention is that it can be provides a novel personal material captured in a jewelry frame.

Other advantages of the present invention will become apparent from the following descriptions, taken in connection with the accompanying drawings, wherein, by way of illustration and example, an embodiment of the present invention is disclosed.

In the preferred embodiment of the present invention, the deciduous dentition, or primary teeth of one or more children, are provided. The dentition is pulverized into dentition particles. In an optional embodiment, the dentition particles are bleached. In an optional embodiment, the dentition particles are etched. In another optional embodiment, the dentition particles are dyed to obtain a desired color. In an optional embodiment, the dentition is pulverized further into a dentition powder.

In a preferred embodiment, a form, or mold, is provided in the design of the jewelry item desired. The dentition particles are mixed with a chemical bonding agent such as dental cement. The mixture of the dentition particles and chemical bonding agent forms a dentition matrix. The matrix is located within the form.

Optionally, an attachment may be located in the matrix to provide a means for attaching the jewelry item to an earring, necklace, bracelet, or the like. Depending on the bonding agent used, specific curing conditions may be recommended to obtain the physical properties desired in the bonded product.

In a preferred embodiment, the matrix is located in a preformed jewelry frame. An example of such an item would be a hollow cross. In this manner, the cured matrix would bond to the jewelry frame, securing it in place geometrically and/or materially. This method provides an interference fit potential with the frame to insure the cured matrix will not dislodge from the frame.

In another preferred embodiment, the deciduous dentition is tumbled into polished dentition particles, larger than a powder. In this embodiment, the dentition particles are mixed or coated with a chemical bonding agent. The mixture of the dentition powder and chemical bonding agent forms the dentition matrix. The matrix is located in a form or pre-formed frame for curing.

BRIEF DESCRIPTION OF THE DRAWINGS

The drawings constitute a part of this specification and include exemplary embodiments to the invention, which may be embodied in various forms. It is to be understood that, in some instances, various aspects of the invention may be shown exaggerated, enlarged or otherwise spatially modified to facilitate an understanding of the invention.

DETAILED DESCRIPTION OF THE INVENTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Humans are diphyodont; they develop two sets of teeth during their lives. The first set of teeth are the deciduous teeth; 20 small teeth also known as baby teeth, milk teeth or primary teeth. Deciduous teeth start developing about two months after conception and typically begin to erupt above the gum line when a baby is six or seven months old. Occasionally a baby is born with one or more deciduous teeth, known as natal teeth. By the time a child is six years old, a second set of 32 larger teeth, called permanent teeth, start to erupt, or push out of the gums, eventually replacing the deciduous teeth.

Figure 1:
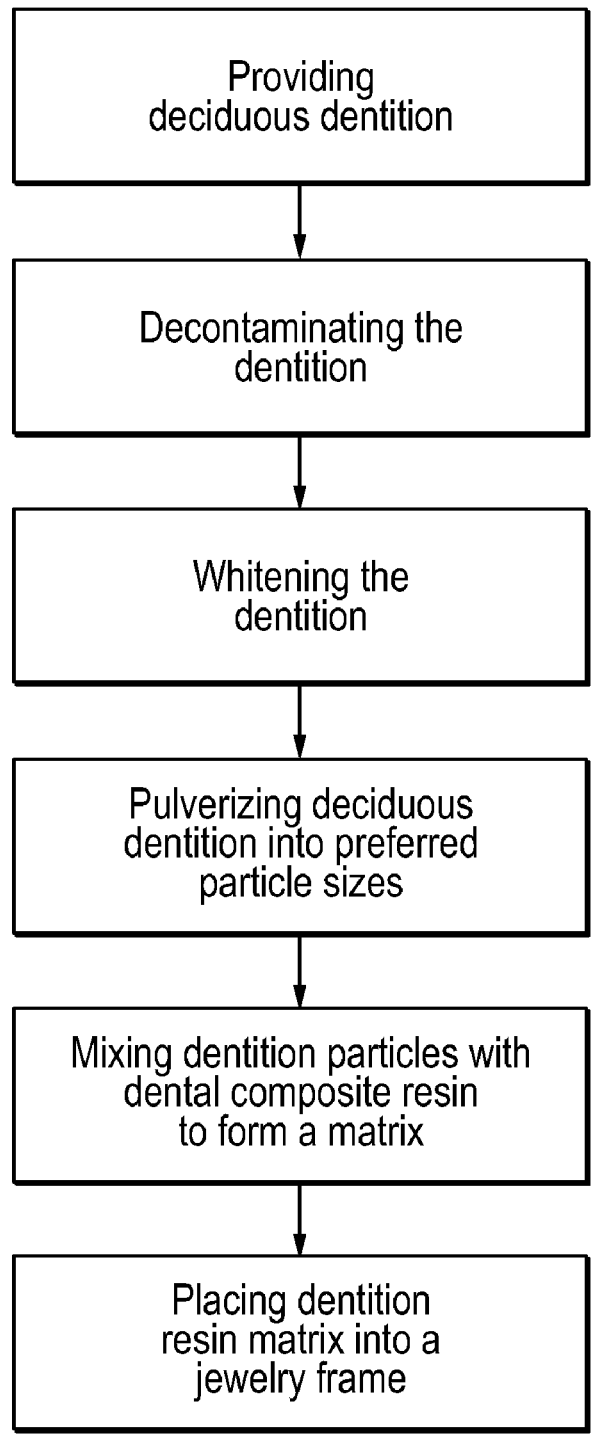
FIG. 1 is an illustration of an example of one embodiment flow chart of the process for making a piece of jewelry made in accordance with a preferred embodiment of the present invention.

FIG. 1 is a flow chart illustrating the steps of creating jewelry in accordance with a preferred embodiment of the present invention. In this Figure, it is seen that the saved dentin may be separately decontaminated and whitened in separate steps. It is also appreciated that it is possible to accomplish this in a single step by bleaching the dentition. This has the benefit a reducing the rupture strength of the dentition. It is possible to perform the disclosed steps in a different order, such as whitening after pulerverizing. It is also possible to add steps, such as for coloring the dentition.

Figure 2:
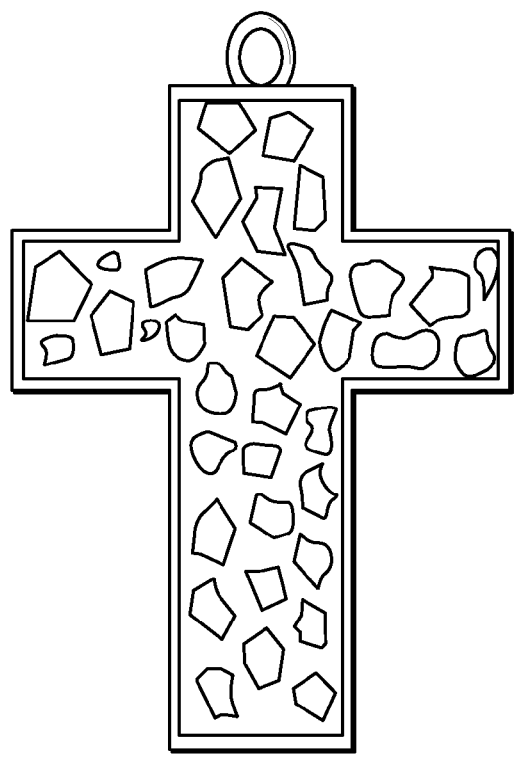
FIG. 2 is an illustration of an example of a piece of jewelry in the shape of a cross with pulverized deciduous dentition cemented in place with composite resin.

FIG. 2 is an illustration of a piece of jewelry made in accordance with a preferred embodiment of the present invention.

Figure 3:
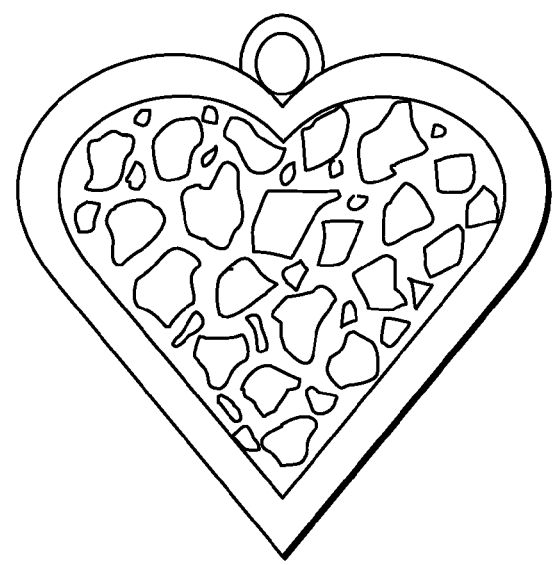
FIG. 3 is an illustration of an example of a piece of jewelry in the shape of a heart with pulverized deciduous dentition cemented in place with composite resin.

FIG. 3 is an illustration of another piece of jewelry made in accordance with a preferred embodiment of the present invention.

In the preferred embodiment of the present invention, the deciduous dentition, or primary teeth of one or more children, are provided. The deciduous dentition is identified and recorded with the person from which they originated and maintained separately from the dentition of others. The dentition should be cleaned of visible blood and debris and kept hydrated in tap water or saline. Extracted teeth, including dentition, are considered biohazardous waste and must be labeled and handled accordingly.

In a preferred embodiment, the provided dentition are decontaminated. Known methods of storing and sterilizing extracted teeth include steam autoclave, freezing, gamma radiation, numerous liquid chemicals, and gaseous chemical.

In a preferred embodiment, the dentition are decontaminated by soaking in a bleach solution or by autoclaving. Bleaching decontaminates and whitens the dentition. Additionally, bleaching may soften the cementum, increasing the dentition's susceptibility to crushing.

For bleaching, the dentition may be placed in a sealed specimen container with a sufficient amount of common household bleach (5.25% or 6%), diluted to approximately 1:10 with tap water. As stated, it will be appreciated that other formulations may be used to obtain a satisfactory result. For example, 10% formalin may be used for decontamination.

Alternatively, the dentition may be heat sterilized, as by autoclaving. It is also possible to both autoclave the dentition and separately bleach it for whiteness, as illustrated in FIG. 1.

The dentition is then partially pulverized into smaller dentition particles. In the preferred embodiment, the particle sizes obtained are between −2 and 2 on the PHI particle scale. This preferred range of particle size retains the natural appearance and recognition of the deciduous dentin, but reduces it to a size small enough to position the particles within the space of a jewelry framework for cementing. In an optional embodiment, the dentition is pulverized into a fine powder form.

The dentition may also be etched with a chemical, such as a phosphoric acid gel. The etching, if performed, roughens the surface of the particles, increasing the surface area and improving the adherence of the dental cement to the particle surfaces. Etching may be performed before or after pulverization. In another optional embodiment, the dentition particles (or powder) are dyed to obtain a desired color.

In a preferred embodiment, a form, or mold, is provided in the design of the jewelry item desired. The dentition particles are mixed with a chemical bonding agent, such as dental cement or dental composite resin. Dental composite resins are types of synthetic resins known in the dental profession as restorative materials or adhesives. These bonding agents are used for the repair of teeth and the construction of artificial teeth and are designed for attachment to tooth enamel.

The mixture of the dentition particles and the chemical bonding agent (dental composite resin) forms a dentition-adhesive matrix. The matrix is placed within the form so as to fill the void of the mold.

Optionally, a jewelry attachment may be located in the matrix to provide a means for attaching the jewelry item to an earring, necklace, bracelet, or the like. Depending on the bonding agent used, specific curing conditions may be recommended to obtain the physical properties desired in the bonded product.

Curing of resins containing a photoinitiator is accelerated by exposure to light, such as ultraviolet light. For example, bonding agents containing compounds, such as amorphous calcium phosphate (ACP) agents, are light-cured bonding adhesives. Precise curing procedures depend on the bonding agent selected.

In a preferred embodiment, the matrix is located in a pre-formed jewelry frame. An example of such an item would be the frame of a religious article, such as a cross. The frame is preferably a hollow metal structure. In this manner, the matrix would bond to the jewelry frame curing, securing it in place geometrically and/or bonding chemically. This method provides an interference fit potential with the frame to insure the cured matrix will not dislodge from the frame.

In an alternative embodiment, the dentition particles are located in the mold first, and the adhesive is then introduced into the mold to fill the voids between the pulverized dentition particles.

In another preferred embodiment, the deciduous dentition is partially crushed into a powder. In this embodiment, the dentition powder is mixed or coated with a chemical bonding agent prior to introduction into the mold. The mixture of the dentition powder and chemical bonding agent forms the dentition matrix, which is then located into a mold form or pre-formed frame for curing.

In another preferred embodiment, the deciduous dentition is tumbled into polished dentition particles, larger than a powder. In this embodiment, the dentition particles are mixed or coated with a chemical bonding agent. The mixture of the dentition powder and chemical bonding agent forms the dentition matrix. The matrix is located in a form or pre-formed frame for curing.

While this invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. A method of creating jewelry, comprising the steps of:
   providing human body components consisting of deciduous dentition;
   non-destructively disinfecting the dentition;
   pulverizing the deciduous dentition into smaller dentition particles;
   providing a jewelry frame;
   mixing the deciduous dentition particles with a bonding agent to form a deciduous dentition matrix paste;
   placing the deciduous dentition matrix paste into the frame; and,
   wherein the matrix paste solidifies to form the jewelry.

2. The method of creating jewelry of claim 1, wherein the pulverized dentition contains at least some particles between −2 and −1 on the PHI scale.

3. The method of creating jewelry of claim 1, further comprising the step of:
   etching the deciduous dentition with a phosphoric acid material.

4. The method of creating jewelry of claim 1, wherein the step of disinfecting further comprises bleaching the deciduous dentition.

5. The method of creating jewelry of claim 1, further comprising the step of:
   dying the pulverized deciduous dentition.

6. The method of creating jewelry of claim 1, further comprising:
   wherein the step of pulverizing the deciduous dentition to a particle size large enough to retain the natural appearance and recognition of deciduous dentin.

7. The method of creating jewelry of claim 1, further comprising:
   wherein the step of disinfecting further comprises autoclaving the deciduous dentition.

8. The method of creating jewelry of claim 1, further comprising:
   polishing the solidified jewelry.

9. The method of creating jewelry of claim 1, further comprising:
   bleaching the dentition particles.

10. The method of creating jewelry of claim 1, wherein in jewelry frame is a hollow metal structure.

11. The method of creating jewelry of claim 1, further comprising:
    locating an attachment in the matrix to provide a means for attaching the jewelry to another jewelry article.

12. A method of creating jewelry, comprising the steps of:
    providing human body components consisting of deciduous dentition;
    non-destructively disinfecting the dentition;
    pulverizing the deciduous dentition into smaller dentition particles;
    mixing the deciduous dentition particles with a bonding agent to form a deciduous dentition matrix paste;
    placing the deciduous dentition matrix paste into a mold; and,
    wherein the matrix paste solidifies to form the jewelry.

13. The method of creating jewelry of claim 12, further comprising:
    locating an attachment in the matrix to provide a means for attaching the jewelry to another jewelry article.

14. The method of creating jewelry of claim 12, wherein the pulverized dentition contains at least some particles between −2 and −1 on the PHI scale.

15. The method of creating jewelry of claim 12, further comprising the step of:
    etching the deciduous dentition with a phosphoric acid material.

16. The method of creating jewelry of claim 12, wherein the step of disinfecting further comprises bleaching the deciduous dentition.

17. The method of creating jewelry of claim 12, further comprising the step of:
    dying the pulverized deciduous dentition.

18. The method of creating jewelry of claim 12, further comprising:
wherein the step of pulverizing the deciduous dentition to a particle size large enough to retain the natural appearance and recognition of deciduous dentin.

19. The method of creating jewelry of claim 12, further comprising:
wherein the step of disinfecting further comprises autoclaving the deciduous dentition.

20. The method of creating jewelry of claim 12, further comprising:
polishing the solidified jewelry.

21. The method of creating jewelry of claim 12, further comprising:
bleaching the dentition particles.

22. A method of creating jewelry, comprising the steps of:
providing human body components consisting of deciduous dentition;
non-destructively disinfecting the dentition;
reducing the deciduous dentition into smaller dentition particles including at least some particles between −2 and −1 on the PHI scale;
mixing the deciduous dentition particles with a bonding agent to form a deciduous dentition matrix paste;
placing the deciduous dentition matrix paste into a frame or mold; and,
wherein the matrix paste solidifies to form the jewelry.

* * * * *

UNITED STATES PATENT AND TRADEMARK OFFICE
CERTIFICATE OF CORRECTION

PATENT NO. : 8,226,877 B2  
APPLICATION NO. : 12/699476  
DATED : July 24, 2012  
INVENTOR(S) : John G. Fischer Page 1 of 1

It is certified that error appears in the above-identified patent and that said Letters Patent is hereby corrected as shown below:

Title page, Item [57] Abstract,  
Line 3, delete "dentin" and insert --dentition--  
Line 5, delete "dentin" and insert --dentition--

In the Specifications  
Column 4,  
Line 12, delete "dentin" and insert --dentition--  
Line 17, delete "pulerverizing" and insert --pulverizing--  
Line 56, delete "dentin" and insert --dentition--

In the Claims  
Column 6, Claim 6  
Line 21, delete "dentin" and insert --dentition--

Column 7, Claim 18  
Line 5, delete "dentin" and insert --dentition--

Signed and Sealed this  
Sixteenth Day of April, 2013

Teresa Stanek Rea  
*Acting Director of the United States Patent and Trademark Office*